United States Patent
Prendergast et al.

(10) Patent No.: US 10,149,747 B2
(45) Date of Patent: *Dec. 11, 2018

(54) ELECTRIC TOOTHBRUSH WITH CONTROLLED SUCTION AND IRRIGATION

(71) Applicant: Dignity Health, San Francisco, CA (US)

(72) Inventors: Virginia Prendergast, Phoenix, AZ (US); Cynthia Kleiman, Scottsdale, AZ (US)

(73) Assignee: Dignity Health, San Francisco, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 15/133,254

(22) Filed: Apr. 20, 2016

(65) Prior Publication Data

US 2016/0228225 A1    Aug. 11, 2016

Related U.S. Application Data

(63) Continuation of application No. 14/388,896, filed as application No. PCT/US2013/034818 on Apr. 1, 2013, now Pat. No. 9,351,816.
(Continued)

(51) Int. Cl.
*A61C 17/22* (2006.01)
*A61C 17/34* (2006.01)
(Continued)

(52) U.S. Cl.
CPC ........ *A61C 17/0208* (2013.01); *A46B 5/0095* (2013.01); *A46B 13/023* (2013.01);
(Continued)

(58) Field of Classification Search
CPC ....... A61C 7/0208; A61C 17/20; A61C 17/22; A61C 17/221; A61C 17/26; A61C 17/34;
(Continued)

(56) References Cited

U.S. PATENT DOCUMENTS 5,544,382 A   8/1996  Giuliani et al.
5,573,398 A   11/1996 Towle et al.
(Continued)

FOREIGN PATENT DOCUMENTS

CN       1554316 A       12/2004
CN       201602908 U     10/2010
(Continued)

*Primary Examiner* — Dung Van Nguyen
(74) *Attorney, Agent, or Firm* — Quarles and Brady LLP

(57) ABSTRACT

An electric toothbrush for use by an operator and capable of being connected to a suction device. The electric toothbrush includes a head with a plurality of bristles, at least one irrigation port, and at least one suction port, and an injection port in fluid communication with the at least one irrigation port. The electric toothbrush also includes a handle with a ventilation port in fluid communication with the at least one suction port, a user interface, and a controller. The ventilation port permits suction from the suction device to the at least one suction port and the controller is configured to actuate at least one of rotation, oscillation, and vibration of the bristles for a preset time period in response to a predetermined feedback from the operator through the user interface.

20 Claims, 2 Drawing Sheets

Related U.S. Application Data

(60) Provisional application No. 61/617,975, filed on Mar. 30, 2012.

(51) Int. Cl.
- *A61C 17/26* (2006.01)
- *A61C 17/02* (2006.01)
- *A61C 17/20* (2006.01)
- *A46B 5/00* (2006.01)
- *A46B 13/02* (2006.01)
- *A46B 15/00* (2006.01)

(52) U.S. Cl.
CPC ...... *A46B 15/0008* (2013.01); *A46B 15/0081* (2013.01); *A61C 17/20* (2013.01); *A61C 17/22* (2013.01); *A61C 17/221* (2013.01); *A61C 17/26* (2013.01); *A61C 17/34* (2013.01)

(58) Field of Classification Search
CPC .. A46B 5/0095; A46B 13/023; A46B 15/0008
See application file for complete search history.

(56) References Cited

U.S. PATENT DOCUMENTS

| | | |
|---|---|---|
| 5,593,304 A | 1/1997 | Ram |
| 5,653,591 A | 8/1997 | Hans |
| 6,119,296 A | 9/2000 | Noe et al. |
| 6,164,967 A | 12/2000 | Sale et al. |
| 6,203,320 B1 | 3/2001 | Williams et al. |
| 6,217,327 B1 | 4/2001 | Bedi |
| 7,306,577 B2 | 12/2007 | Lemoine et al. |
| 2003/0186192 A1* | 10/2003 | Ito .................. A46B 11/063 433/91 |
| 2005/0147460 A1 | 7/2005 | Han et al. |
| 2007/0009857 A1 | 1/2007 | Philp et al. |
| 2009/0111069 A1 | 4/2009 | Wagner |
| 2009/0197220 A1 | 8/2009 | Cindrich |
| 2009/0226241 A1 | 9/2009 | McEwan et al. |
| 2009/0271936 A1 | 11/2009 | Walanski et al. |
| 2010/0124729 A1* | 5/2010 | Liao .................. A46B 11/063 433/80 |
| 2011/0159456 A1 | 6/2011 | Cuevas et al. |
| 2012/0288320 A1 | 11/2012 | Barkhordar |

FOREIGN PATENT DOCUMENTS

| | | |
|---|---|---|
| CN | 201642397 U | 11/2010 |
| JP | S51143565 | 11/1976 |
| JP | 11103938 | 4/1999 |
| JP | H11103938 | 4/1999 |
| JP | 2000139963 A | 5/2000 |
| JP | 2002058537 | 2/2002 |
| JP | 2006180953 A | 7/2006 |
| JP | 2008029659 | 2/2008 |
| WO | 2003099063 | 12/2003 |

* cited by examiner

ELECTRIC TOOTHBRUSH WITH CONTROLLED SUCTION AND IRRIGATION

CROSS-REFERENCE TO RELATED APPLICATIONS

This application is a continuation of U.S. patent application Ser. No. 14/388,896, filed Sep. 29, 2014, which represents the US National Stage of International Application PCT/US2013/034818, filed Apr. 1, 2013 which is based on, claims priority to, and incorporates herein by reference U.S. Provisional Application 61/617,975, filed Mar. 30, 2012.

STATEMENT REGARDING FEDERALLY FUNDED RESEARCH

N/A.

BACKGROUND OF THE INVENTION

The present application is directed to electric toothbrushes. In particular, the present application is directed to electric toothbrushes designed to accommodate or compensate for a wide variety of impediments to oral hygiene, such as restricted range of oral motion or access, or impediments to operation or interaction with traditional cleaning systems and methods, for example, such as may be common with hospitalized people, people living in residential care facilities, bedridden people, and many other patients.

While providing oral hygiene to intubated patients is a technical challenge, doing so is vital for both patients' oral health and overall systemic health and disease prevention. Oral care in an ICU environment is difficult to perform due to physical barriers, such as endotracheal tubes, oral gastric tubes, and bite blocks, that hamper access to the oral cavity. A patient's inability to swallow or expel toothpaste and/or rinsing fluid presents yet another obstacle in providing oral care in such environments.

Various oral care protocols are provided for ICU environments, though little evidence supports implementation of such protocols. For instance, manual toothbrushes have been proposed as the ideal method for promoting oral hygiene of orally intubated patients. Even though foam swabs appear to be inferior in removing oral debris and dried secretions compared to the recommended manual toothbrush, many ICU nurses still use foam swabs since they require less dexterity to manipulate than a toothbrush. Using foam swabs and allowing additional build-up of oral debris and dried secretions can lead to deterioration in a patient's oral health and increased incidence of pneumonia.

Thus, despite the importance of providing effective oral hygiene for ICU patients, effective, easy to use oral care tools for hospital or institutional environments are lacking. This is a major factor as to why oral care protocols, as discussed above, are often incorrectly implemented or ignored altogether.

Therefore, it would be desirable to provide a toothbrush that minimizes the manual dexterity necessary to clean the teeth and oral cavity of an intubated, hospitalized, or other patient or person in residential care facilities. It would also be desirable to provide a toothbrush capable of instillation of rinsing agents and application of suction, so that a single tool may be used to provide effective oral care.

SUMMARY OF THE INVENTION

The present invention overcomes the aforementioned drawbacks by providing an electric toothbrush designed to accommodate or compensate for a wide variety of impediments to oral hygiene, such as may be common for people that are hospitalized, people that are living in residential care facilities, and/or people that are debilitated. The electric toothbrush includes a rotating and/or oscillating low profile head, at least one suction port for vacuum suction, at least one irrigation port for instillation of a rinsing fluid, and a user interface. The handle of the toothbrush provides access to the user interface configured to control mechanical brushing operation of the bristles and to control the suction port, as well as an injection port capable of receiving a syringe to transfer rinsing fluid through the toothbrush and out the irrigation port.

According to one implementation of the invention, an electric toothbrush is provided for use by an operator and is capable of being connected to a suction device. The electric toothbrush includes a head including a plurality of bristles, at least one irrigation port, and at least one suction port. The electric toothbrush also includes an injection port in fluid communication with the at least one irrigation port. The electric toothbrush further includes a handle with a ventilation port, a user interface, and a controller. The ventilation port is in fluid communication with the at least one suction port, is configured to be coupled to the suction device, and permits suction from the suction device to the at least one suction port. The user interface is configured to receive feedback from the operator, and the controller is configured to actuate at least one of rotation, oscillation, and vibration of the bristles for a preset time period in response to a predetermined feedback from the operator through the user interface.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Generally, the present invention provides an electric toothbrush designed to accommodate or compensate for a wide variety of impediments to oral hygiene. The electric toothbrush includes a rotational and/or oscillating low profile head, at least one suction port for vacuum suction, at least one irrigation port for instillation of a rinsing fluid, and a user interface. The handle of the toothbrush provides access to the user interface so that the electric toothbrush can be controlled without undue dexterity or cumbersome interactions.

Figure 1:
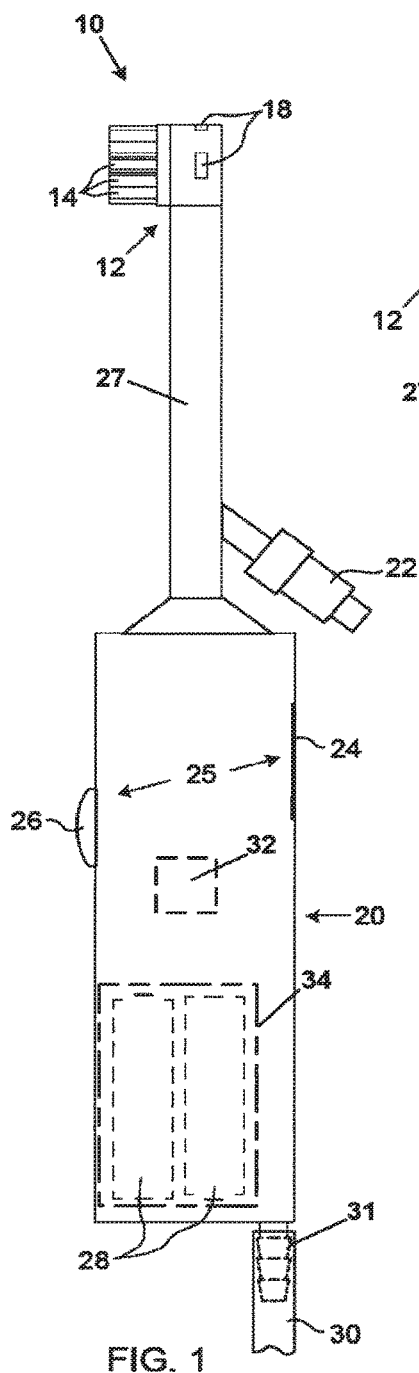
FIG. 1 is a side view of an electric toothbrush in accordance with and/or for use with the present invention.
Figure 2:
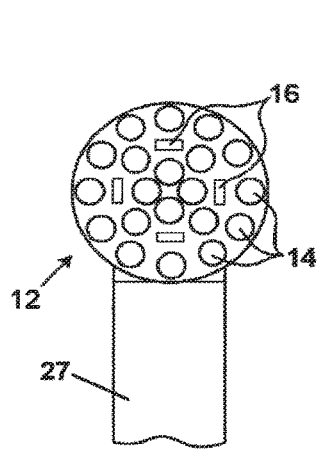
FIG. 2 is a partial front view of the electric toothbrush of FIG. 1.
Figure 3:
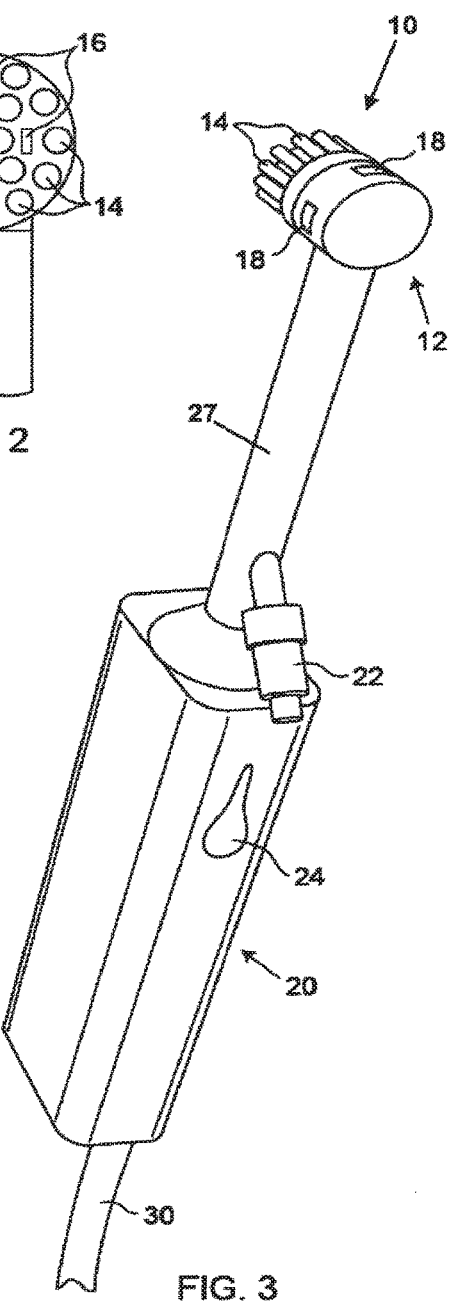
FIG. 3 is a perspective view of the electric toothbrush of FIG. 1.

FIGS. 1-3 illustrate an electric toothbrush 10 according to one implementation of the invention. The electric toothbrush 10 can be used to provide oral care despite any of a wide variety of impediments to oral hygiene, such as may be common for people that have been hospitalized, people living in residential care facilities, and/or people that have been debilitated. The electric toothbrush 10 can include a head 12 with bristles 14, at least one irrigation port 16, and at least one suction port 18, and a handle 20 with an injection port 22 and a user interface 25 configured to receive feedback from an operator. In some implementations, as shown in FIGS. 1 and 3, the injection port 22 is separate from the handle 20 and is positioned along a post 27 that connects the head 12 and the handle 20. In addition, as shown in FIGS. 1 and 3, the user interface 25 can include a timer button 26 for initiating an internal timer. The handle 20 can also include a ventilation port 24, which may be considered part of the user interface 25. The electric toothbrush 10 can significantly improve oral health by removing dental plaque, oral debris, and oral biofilm, while also stimulating gingival tissues and providing oral moisturizers in patients who are hospitalized, in residential treatment facilities, or otherwise unable to perform oral self hygiene.

Brushing, irrigation, and suction by the toothbrush 10 can all be provided through the head 12. Providing all three actions on a single tool makes it easier for an operator (for example, a nurse or other care giver that may need to simultaneously attend to multiple tasks and cannot dedicate full attention and all available limbs) to perform oral care on a patient. In this regard, the present invention stands in contrast to conventional oral care techniques that include separate suction tubes, rinsing injectors, and toothbrushes. In one implementation of the invention, the head 12 can have a low profile (for example, can be rounded, flatter, with shorter bristles 14, and/or substantially smaller than common manual toothbrush heads). This allows for easier insertion into a patient's mouth, especially for patients who have difficulties opening their mouths due to a restricted range of oral motion or have physical barriers, such as endotracheal tubes, oral gastric tubes, and bite blocks, that hamper access to the patient's oral cavity. In addition, the head 12 and/or the post 27 can be constructed of a pliable material (for example, instead of a hard plastic), which can help reduce damage to the patient's oral cavity during use.

In some implementations, the head 12 (or just the bristles 14) can oscillate, rotate, and/or vibrate during operation. Due to this mechanical action of the head 12, the need for manual dexterity on behalf of the operator is significantly decreased in comparison to using a manual toothbrush. In addition, as shown in FIG. 2, the irrigation ports 16 can be interspersed between the bristles 14 on the front surface of the head 12 to instill an irrigant, or rinsing agent or fluid, into the patient's mouth near the head 12. The suction ports 16 can be located along edges or side surfaces of the head 12 to provide on-demand suction of oral waste (such as the rinsing agent, toothpaste, saliva, and/or other oral debris). Some implementations of the invention may provide the bristles 14, the irrigation ports 16, and the suction ports 18 in relative arrangements other than what is shown in FIGS. 1-3.

Brushing, irrigation, and suction, as described above, can each be separately controlled through the handle 20 without undue dexterity or cumbersome interactions. As such, the operator is further capable of controlling and operating the toothbrush 10 primarily using a single hand, which is not possible with many traditional systems. With respect to irrigation, the injection port 22, located at or near the handle 20, is in fluid communication with the irrigation ports 16 on the head 12 (for example, through internal channels or tubing routed through the post 27). A syringe filled with the rinsing agent (not shown) can be coupled to the injection port 22 so that the operator can expel some or all of the contents of the syringe through the injection port 22, and therefore also through the irrigation ports 16. The injection port 22 and the syringe can be an improvement over other toothbrushes that include liquid reservoirs for rinsing agents because the liquid reservoirs can more easily harbor bacteria within the toothbrush. The injection port 22 and the syringe also allow on-demand use of additional rinsing agent (for example, via additional syringes) while the toothbrush 10 is in use.

With respect to suction, the handle 20 can be coupled to a vacuum/suction device (not shown) by suction tubing 30 attached to a suction connection 31 of the handle 20, as shown in FIG. 1. Internal tubing can be routed from the suction connection 31, through the handle 20, through the post 27, and to the suction ports 18 on the head 12. The ventilation port 24 is, for example, a tear drop-shaped port extending through the handle 20 and into the tubing routed through the handle 20. As shown in FIGS. 1 and 3, the ventilation port 24 can be located along the handle 20 so that an operators thumb can be used to selectively uncover or cover the ventilation port 24 and therefore selectively provide or stop suction through the suction ports 18, respectively, again, using a single hand. In this regard, the ventilation port 24 can function as a further component in an overall user interface 25 that can be readily accessed and communicated with through the handle 20. In some designs, the ventilation port 24 can be located at other positions along the handle 20 so that an operator's finger (that is, other than the operator's thumb) can be used to selectively uncover or cover the ventilation port 24. For example, in such designs, the ventilation port can be located directly above or below the timer button 26.

As described above, the injection port 22 and the ventilation port 24 provide separate, simple controls for providing suction and irrigation through the handle 20. In other implementations of the invention, the toothbrush 10 can provide constant suction, or can include a different arrangement, such as a switch actuated or electronic control, to selectively provide or stop suction. Further, the toothbrush 10 can include different arrangements or connectors on the injection port 22 to account for different syringe heads or other types of injection equipment (for example, to accommodate screw-type connections, luer-lock type connections, needleless access connections, etc.).

With respect to brushing, mechanical operation of the bristles 14 can be controlled through the handle 20. For example, the handle 20 can include an on/off switch (not shown) as part of the user interface 25 so that an operator can turn on and shut off mechanical operation of the bristles 14, again, by interacting with the single handle 20, such as can be achieved using a single hand. The on/off switch can be connected to an internal controller 32 located within the handle 20. The internal controller 32 can be electrically coupled to the head 12 (for example, via electrical connections routed through the post 27) to actuate mechanical operation of the head 12.

Alternatively, or in addition to the on/off switch, the handle 20 can include the timer button 26, as shown in FIG. 1, connected to the internal controller 32. The internal controller 32 can include an internal timer and activates mechanical operation of the bristles 14 for a preset time period when the timer button 26 is pressed. More specifically, pressing the timer button 26 causes the controller 32 to actuate mechanical operation of the head 12 and/or the bristles 14 (that is, rotation, oscillation, and/or vibration) for two minutes, in accordance with current outpatient oral care standards, or another set time. In other words, the controller 32 is configured to start the internal timer in response to predetermined feedback from the operator (that is, pressing the timer button 26), and the internal timer is configured to expire when the preset time period, such as two minutes, has passed. The controller 32 is configured to actuate mechanical operation of the head 12 when the internal timer is started and to stop actuation when the internal timer is expired. This can provide a standardized time that the operator should brush the patient's teeth, thus helping implement standardized protocols.

Also, the timer, the controller 32, and/or the mechanical parts for rotating and/or oscillating the bristles 14 can be powered by batteries 28 located inside the handle 20, for example, in a user-accessible battery compartment 34. The batteries 28 can be replaceable, in which case the handle 20 can include a removable cover (not shown) for insertion and removal of the batteries 28 within the batter compartment 34. In some implementations, the batteries 28 can be rechargeable, in which case the handle 20 can include charging leads and can be plugged into a charging dock, or can include a charging port for receiving a charging plug.

Figure 4:
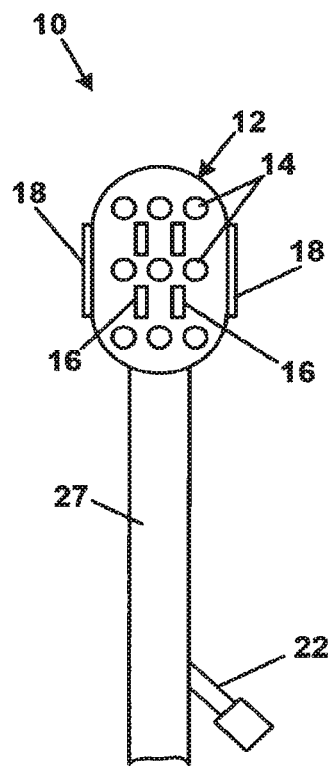
FIG. 4 is a partial front view of an electric toothbrush in accordance with and/or for use with the present invention.
Figure 5:
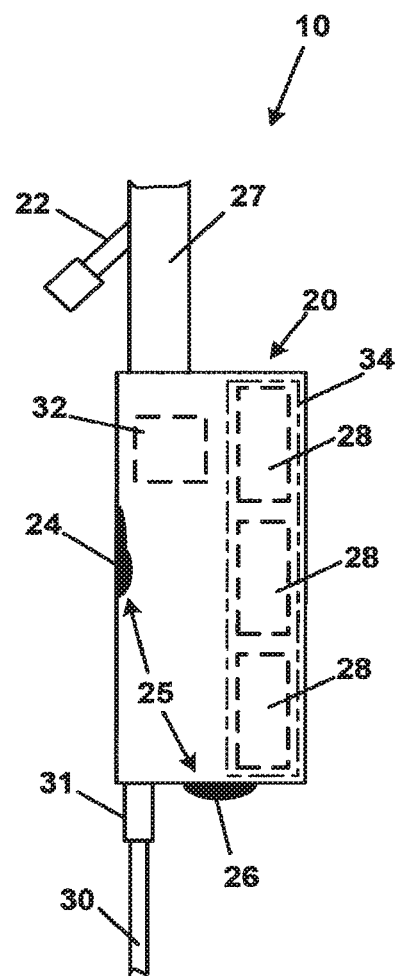
FIG. 5 is a partial side view of the electric toothbrush of FIG. 4.

As described above, the head 12 can have a substantially low profile and can be substantially tapered from the handle 20. The low profile and tapered design can allow for easier use by an operator to provide oral care to a subject or patient. In one example, the low profile can allow for an operator to better provide oral care to an intubated patient. FIGS. 1-3 illustrate the head 12 with a round profile. FIGS. 4-5 illustrate an electric toothbrush according to another implementation of the invention. The electric toothbrush 10 of FIGS. 4-5 can include similar components as the electric toothbrush of FIGS. 1-3, but with a more oval or rectangular profile head 12. In some implementations, mechanical brushing operations can include circular or lateral oscillation of the bristles 14 (that is, with either the round profile of FIG. 2 or the rectangular profile of FIG. 4). In addition, the electric toothbrush 10 of FIGS. 4-5 includes a different shaped battery storage compartment 34 and different user interface 25 placement.

One or more of the components described above can be disposable for single-time or multiple-time use. For example, in one implementation of the invention, the head 12 and the handle 20 can be removably coupled together, having relative connecting portions, so that the head 12 can be detached from the handle 20 and disposed of after use and a new, clean head 12 can be connected to the handle 20 during the next use. In some implementations, the head 12 and the post 27 can be one integral piece (that is, the post 27 can be part of the head 12) and the post 27 can be removably coupled to the handle 20 to allow detachment and replacement of the head 12 after one or more uses. The suction tubing 30 can also be detachable from the handle 20, as shown in FIG. 1, so that the electric toothbrush 10 can be used with different suction devices (for example, so that the operator only needs to transport the electric toothbrush 10, rather than both the electric toothbrush 10 and the vacuum/suction device).

Furthermore, other components can be attached to the handle 20 and/or the head 12 for additional oral care, such as a replaceable tongue scraper attachment (not shown). In some designs, a rear surface of the head 12 (that is, relative to the front surface including the bristles 14 and the irrigation ports 14 and the side surface including the suction ports 18, as shown in FIGS. 1-5) can include a tongue scraper portion. In addition, some implementations of the invention can include different combinations of the components described above. For example, the electric toothbrush 10 can be a suction-only toothbrush, including only the suction ports 18 rather than both the suction ports 18 and the irrigation ports 16, for use with patients requiring only suction assistance during oral care.

The present invention has been described in terms of one or more preferred embodiments, and it should be appreciated that many equivalents, alternatives, variations, and modifications, aside from those expressly stated, are possible and within the scope of the invention.

The invention claimed is:

1. An electric toothbrush for use by an operator and capable of being connected to a suction device, the electric toothbrush comprising:
 a head including a plurality of bristles;
 an irrigation port;
 an injection port in fluid communication with the irrigation port;
 a suction port;
 a suction connection in fluid communication with the suction port and configured to be coupled to the suction device;
 a ventilation port in fluid communication with the suction port and the suction connection, the ventilation port permitting suction from the suction device to the suction port; and
 a handle coupled to the head and including a user interface configured to receive feedback from the operator, the handle configured to actuate at least one of rotation, oscillation, and vibration of the plurality of bristles in response to a predetermined feedback from the operator through the user interface.

2. The electric toothbrush of claim 1, wherein the handle includes a controller configured to actuate at least one of rotation, oscillation, and vibration of the plurality of bristles in response to the predetermined feedback from the operator through the user interface.

3. The electric toothbrush of claim 2, wherein the controller is further configured to actuate at least one of rotation, oscillation, and vibration of the plurality of bristles for a preset time period in response to the predetermined feedback from the operator through the user interface.

4. The electric toothbrush of claim 3, wherein the controller includes an internal timer configured to start in response to the predetermined feedback from the operator through the user interface and to expire when the preset time period has passed, and the controller is configured to actuate at least one of rotation, oscillation, and vibration of the plurality of bristles when the internal timer is started and to stop actuation when the internal timer is expired.

5. The electric toothbrush of claim 3, wherein the preset time period is two minutes.

6. The electric toothbrush of claim 1, wherein the ventilation port is configured to control suction from the suction device to the suction port based on the operator covering and releasing the ventilation port; and wherein the ventilation port and the user interface are positioned relative to each other to accommodate single-handed operation of the electric toothbrush.

7. The electric toothbrush of claim 1, wherein the irrigation port is located one of on the head and adjacent to the plurality of bristles.

8. The electric toothbrush of claim 1 and further comprising tubing routed from the suction connection to the suction port, wherein the ventilation port extends into the tubing.

9. The electric toothbrush of claim 1, wherein the injection port is configured to be connected to a syringe.

10. The electric toothbrush of claim 9, wherein the injection port includes a luer-lock type connection configured to be connected to a syringe.

11. The electric toothbrush of claim 1, wherein the ventilation port is tear-drop shaped.

12. The electric toothbrush of claim 1, wherein the user interface includes a button connected to the controller.

13. The electric toothbrush of claim 1, wherein the head includes one of a round profile and a rectangular profile.

14. The electric toothbrush of claim 1 and further including a post that couples the head to the handle.

15. The electric toothbrush of claim 14, wherein at least one of the ventilation port, the head, the post, and the handle are disposable.

16. The electric toothbrush of claim 14, wherein the head and the post are constructed of a pliable material.

17. The electric toothbrush of claim 16, wherein the injection port is in fluid communication with the irrigation port through an internal channel of the post.

18. The electric toothbrush of claim 1, wherein the handle includes a battery compartment.

19. The electric toothbrush of claim 1, and further comprising a tongue scraper.

20. The electric toothbrush of claim 1, wherein the handle supports the ventilation port.

* * * * *